United States Patent [19]

Leupold et al.

[11] 4,128,575
[45] Dec. 5, 1978

[54] PROCESS FOR THE MANUFACTURE OF GLYCOLIC ACID OR ITS ESTERS

[75] Inventors: Ernst I. Leupold, Westerfeld; Hans-Jürgen Arpe, Kelkheim, both of Fed. Rep. of Germany

[73] Assignee: Hoechst Aktiengesellschaft, Frankfurt am Main, Fed. Rep. of Germany

[21] Appl. No.: 853,210

[22] Filed: Nov. 14, 1977

[30] Foreign Application Priority Data

Nov. 15, 1976 [DE] Fed. Rep. of Germany ......... 265207
Nov. 15, 1976 [DE] Fed. Rep. of Germany ....... 2652003
Sep. 15, 1977 [DE] Fed. Rep. of Germany ....... 2741505

[51] Int. Cl.$^2$ ............................................. C07C 59/06
[52] U.S. Cl. .................................... 562/579; 560/185; 560/187
[58] Field of Search .................... 260/535 R; 560/179, 560/185, 187

[56] References Cited

U.S. PATENT DOCUMENTS

| | | | |
|---|---|---|---|
| 2,211,624 | 8/1940 | Loder et al. | 260/535 R |
| 2,686,797 | 8/1954 | Bersworth et al. | 260/535 R |
| 3,754,028 | 8/1973 | Lapporte et al. | 260/535 R |
| 4,052,452 | 10/1977 | Scardigno | 260/535 R |

FOREIGN PATENT DOCUMENTS

| | | | |
|---|---|---|---|
| 508383 | 6/1939 | United Kingdom | 260/535 |
| 879652 | 10/1961 | United Kingdom | 260/535 |

*Primary Examiner*—Paul J. Killos
*Attorney, Agent, or Firm*—Curtis, Morris & Safford

[57] ABSTRACT

Glycolic acid or the esters thereof are prepared by reacting paraformaldehyde or trioxane or a mixture thereof with formic acid or a formic acid ester in the liquid phase at a temperature of from 70° to 200° C in the presence of a strongly acidic catalyst.

6 Claims, No Drawings

PROCESS FOR THE MANUFACTURE OF GLYCOLIC ACID OR ITS ESTERS

This invention relates to a process for the manufacture of glycolic acid or its esters from paraformaldehyde or trioxane and formic acid or the esters thereof in the liquid phase in the presence of strongly acidic catalysts.

It is known to react solutions of formaldehyde or its linear and cyclic polymers (particularly paraformaldehyde and trioxane) with carbon monoxide to obtain glycolic acid or with carbon monoxide and an alcohol to obtain a glycolic acid ester. Because of the low reactivity of carbon monoxide, the reaction is generally carried out at a temperature of approximately 200° C. under a pressure of about 700 bars when glycolic acid is produced and 400 bars for the esters thereof.

The high reaction pressure and the use of a gaseous reaction component which, especially with carbon monoxide, requires considerable expenditure pertaining to apparatus, is an important technological and thus economic disadvantage of the known processes as compared to processes carried out in liquid phase which do not cause such problems.

The present invention provides a process for the manufacture of glycolic acid or its esters which comprises reacting paraformaldehyde or trioxane or a mixture thereof with formic acid or an ester thereof in the liquid phase at a temperature of from 70° to 200° C. in the presence of strongly acidic catalysts.

Surprisingly, the process of the invention has decisive advantages over the methods hitherto proposed. The use of formic acid or the esters thereof according to the invention allows of carrying out the process at atmospheric pressure or, if the reaction is carried out at a temperature above the boiling point of formic acid or of the respective formic acid ester, at a relatively low excess pressure of 20 to 30 bars. A still higher pressure of 200 bars, for example, is also possible, but in general it does not offer any advantage. Hence, expensive investments necessary for a high pressure process are superfluous when, according to the invention, formic acid or an ester thereof is reacted with paraformaldehyde or trioxane instead of carbon monoxide or carbon monoxide and an alcohol. Extensive safety measures as required in a process using carbon monoxide can also be dispensed with.

As catalysts there can be used, on principle, all strongly acidic compounds as the velocity of the reactions

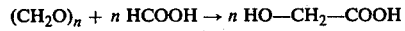
$(CH_2O)_n + n\ HCOOH \rightarrow n\ HO-CH_2-COOH$

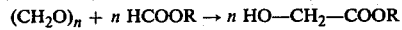
$(CH_2O)_n + n\ HCOOR \rightarrow n\ HO-CH_2-COOR$ distinctly depends on the acid strength of the catalyst. Especially suitable are sulfuric acid and/or organic sulfonic acids such as p-toluene-sulfonic acid, benzene-sulfonic acid, α- or β-naphthalene-sulfonic acid, methanesulfonic acid, ethane-sulfonic acid, hexane-sulfonic acid, or trifluoromethane sulfonic acid.

The molar ratio of paraformaldehyde and/or trioxane (calculated on their formaldehyde content) to formic acid or the formic acid ester is not critical. Preferably, a ratio in the range of from 0.5 to 2 is chosen. To produce glycolic acid the formic acid can be used in pure form or in the form of a solution in acetic acid as obtained as by-product in some industrial processes for the manufacture of acetic acid. It is likewise possible to use other solvents, for example hydrocarbons or ethers. If acetic acid is present in the reaction mixture, acetylglycolic acid is formed in addition to glycolic acid according to the equation $$HO-CH_2-COOH + CH_3COOH \rightleftharpoons CH_3COOCH_2COOH + H_2O$$

which can be transformed into glycolic acid by saponification according to usual methods.

Preferably, an organic sulfonic acid that is liquid at room temperature, for example methane-sulfonic acid, is used as solvent and simultaneously acts as the necessary acidic catalyst. It is, of course, also possible to use, besides the organic sulfonic acid, a further acidic catalyst, but generally this is not necessary.

In the process for the manufacture of glycolic acid esters according to the invention, on principle, all formic acid esters of the formula HCOOR are suitable. Especially suitable radicals R are alkyl, cycloalkyl and aralkyl having up to 8 carbon atoms, for example methyl, ethyl, propyl, i-propyl, n-butyl, isobutyl, tert-butyl, cyclohexyl, benzyl, n-octyl and 2-ethylhexyl.

The reaction is carried out at a temperature of from 70° to 200° C., preferably 90° to 180° C.

The amount of catalyst to be used can vary within wide limits. If, in the production of glycolic acid, the catalyst is identical with the solvent (organic sulfonic acid), it is used in 1 to 10 times, preferably 2 to 5 times the amount of formic acid. With a solvent other than an organic sulfonic acid in the production of glycolic acid or when a glycolic acid ester is produced the amount of catalyst ranges, in general, from 0.1 to 100 mol %, preferably 5 to 50 mol %, calculated on the formic acid or formic acid ester used.

To carry out the process of the invention the mixture of paraformaldehyde and/or trioxane, formic acid or formic acid ester, catalyst and solvent, if any, is heated at atmospheric pressure or slight excess pressure. At a reaction temperature above 100° C. an excess pressure of 20 to 30 bars proved to be suitable to prevent the formic acid from evaporating from the liquid phase.

Correspondingly, at a reaction temperature above the boiling point of the respective formic acid ester an excess pressure of up to 50 bars is advantageous to prevent the ester from evaporating from the liquid phase. The presence of an inert gas, for example nitrogen, is possible.

The process of the invention can be carried out in any apparatus suitable for reactions in the liquid phase with or without the application of excess pressure, for example in an enameled autoclave.

When glycolic acid is produced the reaction mixture can be worked up according to several methods, depending on the type of solvent used and the intended use of the glycolic acid. When the reaction is carried out in the presence of liquid organic sulfonic acids as solvent, which is preferred, almost the entire amount of glycolic acid is obtained in the form of its linear polyester, i.e. sparingly soluble polyglycolic acid (polyglycolide), which can be isolated from the reaction mixture without difficulty by filtration or another usual separating method. Pure polyglycolic acid can be obtained, for example, by washing with methanol. Without much expenditure this acid can be split to give monomeric glycolic acid by heating in the presence of water. The filtrate, essentially consisting of the organic sulfonic acid and a minor proportion of monomeric glycolic acid can be used again as solvent in the process of the invention.

When the reaction is carried out in the presence of a solvent other than an organic sulfonic acid or even without solvent, the reaction mixture may be heated with an alcohol, for example methanol or ethanol. The glycolic acid ester formed is distilled off and then hydrolized. Alternatively, the acid catalyst in the reaction mixture is neutralized with aqueous sodium hydroxide solution, whereby an aqoeous glycolic acid solution is obtained which, besides free glycolic acid, always contains a certain proportion of polyglycolide according to the following equilibrium:

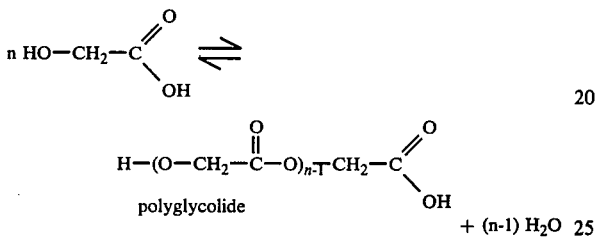

By the addition of water this equilibrium can be shifted essentially to the side of monomeric glycolic acid.

Aqueous glycolic acid solutions of this type are used, on a large scale, in textile, leather and fur finishing, for metal cleaning, metal plating and for the disinfection of dairy apparatus. Further fields of application of glycolic acid are the cleaning of drinking water wells and the adjustment of the pH of cooling waters with a view to reduce the formation of incrustations in heat exchangers.

In the case of a glycolic acid ester being produced the reaction mixture can be worked up according to known methods, for example the glycolic acid ester formed is directly distilled off from the reaction mixture.

Glycolic acid esters are used for many technological applications. By hydrolysis of the esters glycolic acid can be obtained in very pure form.

The hydrogenolysis of the methyl ester is used in industry to produce glycol. Glycolic acid n-butyl ester is a commercial varnish improving agent. Quite generally, glycolic acid esters are characterized by an excellent dissolving power for polymers, copolymers, nitrocellulose, cellulose ethers, celluloid, chlorinated rubber and resins.

The following examples illustrate the invention.

EXAMPLE 1

In an enameled autoclave a mixture of 6 g of paraformaldehyde (= 0.2 mol of $CH_2O$), 0.2 mol (9.2 g) of formic acid and 0.5 ml of $H_2SO_4$ was heated for 3 hours at 140° C. under a nitrogen pressure of 10 bars. The cooled reaction mixture contained 0.14 mol of total glycolic acid (sum of free and polymeric glycolic acid), corresponding to a yield of 69 mol %, calculated on the paraformaldehyde and formic acid used.

EXAMPLE 2

In a flask with stirrer, reflux condenser and inlet tube 46 g (1 mol) of formic acid was added at 90° C. over a period of 5 hours to 30 g (0.33 mol) of trioxane (= 1 mol $CH_2O$) and 25 ml of 98% $H_2SO_4$. Stirring of the reaction mixture was continued for another hour, whereupon the mixture was cooled. Analysis indicated 0.78 mol of total glycolic acid, corresponding to a yield of 78 mol %, calculated on the starting components used.

EXAMPLES 3 to 6

The following experiments were carried out in glass tubes sealed by melting. In each experiment 0.6 g of paraformaldehyde (20 mmols of $CH_2O$), 0.92 g (20 mmols) of formic acid and the amount of concentrated sulfuric acid indicated in the following table were heated for 4 hours. After said period, the yield of total glycolic acid and the proportion of monomeric glycolic acid was determined by analysis.

| Example | $H_2SO_4$ (ml) | temp. (° C) | yield (mol %) total glycolic acid | yield (mol %) free glycolic acid |
|---|---|---|---|---|
| 3 | 0.5 | 100 | 84 | 20 |
| 4 | 0.5 | 110 | 91 | 45 |
| 5 | 0.05 | 120 | 27 | 18 |
| 6 | 0.05 | 160 | 81 | 80 |

EXAMPLES 7 to 9

The experiments were carried out as described in Examples 3 to 6 with the exception that different catalysts were used.

| Example | catalyst (10 mmols) | temp. (° C) | yield of total glycolic acid (mol %) |
|---|---|---|---|
| 7 | $H_2SO_4$ | 110 | 91 |
| 8 | $CF_3SO_3H$ | 110 | 92 |
| 9 | $CH_3SO_3H$ | 110 | 70 |

EXAMPLE 10

In a glass tube sealed by melting a mixture of 1.2 g of paraformaldehyde (= 40 mmols of $CH_2O$) 0.92 g (20 mmols) of formic acid and 0.5 ml of concentrated sulfuric acid were heated for 4 hours at 110° C. The reaction mixture contained 19.9 mmols of total glycolic acid, corresponding to a yield of 99 mol %, calculated on the formic acid used.

EXAMPLE 11

In a flask with stirrer, reflux condenser and inlet tube a 25% solution of formic acid in acetic acid containing 20 g (0.45 mol) of formic acid was added at 100° C. over a period of 4 hours to 12 g of paraformaldehyde (= 0.4 mol $CH_2O$) and 5 ml of concentrated sulfuric acid. Analysis indicated 0.17 mol of acetylglycolic acid, corresponding to a yield of 43 mol %, calculated on the paraformaldehyde used, and 0.16 mol of total glycolic acid, corresponding to a yield of 39 mol %, calculated on the paraformaldehyde used. The acetylglycolic acid could be readily hydrolized by heating it with an excess of aqueous NaOH, the mixture of hydrolysis then contained 0.33 mol of total glycolic acid.

EXAMPLE 12

In a glass flask with reflux condenser 6 g of paraformaldehyde (= 0.2 mol $CH_2O$) and 9.2 g (0.2 mol) of formic acid in 20 ml of methane-sulfonic acid were heated for 2 hours at 100° C. After cooling, the colorless precipitate was filtered off, washed with methanol and dried. 10.5 g of polyglycolic acid (polyglycolide) were obtained. The filtrate still contained 1.1 g of total glycolic acid (sum of free and polymeric glycolic acid). It could be used again as solvent without further purification.

5 g of the polyglycolic acid obtained were heated for 30 minutes to 120° C. together with 5 g of water. A glycolic acid solution of 57% strength was obtained.

EXAMPLE 13

In a glass tube sealed by melting 0.6 g of paraformaldehyde (20 mmols of $CH_2O$), 1.2 (20 mmols) of formic acid methyl ester and 0.5 ml of concentrated sulfuric acid were heated for 5 hours at 90° C. In the reaction mixture 0.9 g of glycolic acid methyl ester could be detected, corresponding to a yield of 50 mol %. The reaction mixture further contained 0.38 g of glycolic acid and 0.4 g of methoxyacetic acid methyl ester ($CH_3$—O—$CH_2$—$COOCH_3$).

EXAMPLE 14

In the manner described in Example 13, 0.6 g of paraformaldehyde, 1.2 g of formic acid methyl ester and 0.9 ml of trifluoromethane-sulfonic acid were heated for 1 hour to 120° C. The reaction mixture contained 1.1 g of glycolic acid methyl ester, corresponding to a yield of 61 mol %, calculated on the starting compounds used.

EXAMPLE 15

In an enamelded autoclave 12 g of trioxane (= 0.4 mol of $CH_2O$), 41 g (0.4 mol) of formic acid n-butyl ester and 1.2 ml of methane-sulfonic acid were heated for 1 hour to 157° C. The reaction mixture contained 17.5 g of glycolic acid n-butyl ester, corresponding to a yield of 33 mol %.

EXAMPLE 16

In a flask with stirrer 12 g of paraformaldehyde (= 0.4 mol of $CH_2O$), 63.3 g (0.4 mol) of formic acid n-octyl ester and 10 ml of concentrated sulfuric acid were heated for 1 hour to 110° C. The reaction mixture contained 18.1 g of glycolic acid n-octyl ester, corresponding to a yield of 24 mol %.

We claim:

1. Process for the manufacture of glycolic acid or an ester thereof which comprises reacting paraformaldehyde or trioxane or a mixture thereof with formic acid or a formic acid ester in the liquid phase at a temperature of from 70° to 200° C. in the presence of a strongly acidic catalyst.

2. The process of claim 1, wherein sulfuric acid or an organic sulfonic acid is used as catalyst.

3. The process of claim 1, wherein in the manufacture of glycolic acid an organic sulfonic acid which is liquid at room temperature is used as solvent and as catalyst, the polyglycolic acid separating in the reaction in the form of a precipitate is isolated and then split to give monomeric glycolic acid by heating the precipitate in the presence of water.

4. The process of claim 3, wherein the organic sulfonic acid is methane-sulfonic acid.

5. The process of claim 1, wherein the reaction is carried out at a temperature of from 90° to 180° C.

6. The process of claim 1, wherein in the manufacture of glycolic acid acetic acid is used as solvent for the formic acid.

* * * * *